United States Patent [19]

Rodari

[11] Patent Number: 4,508,117

[45] Date of Patent: Apr. 2, 1985

[54] APPARATUS FOR ARTIFICIAL PULMONARY VENTILATION DURING ANAESTHESIA AND RESUSCITATION

[75] Inventor: Gianpiero S. Rodari, Bussero, Italy

[73] Assignee: Soxil S.p.A., Milan, Italy

[21] Appl. No.: 417,478

[22] Filed: Sep. 13, 1982

[51] Int. Cl.³ .............................................. A61M 16/00
[52] U.S. Cl. ........................... 128/204.21; 128/204.25; 128/205.24; 137/624.15
[58] Field of Search ...................... 128/205.24, 204.18, 128/204.21, 205.18, 204.25; 137/624.15

[56] References Cited

U.S. PATENT DOCUMENTS

| | | | |
|---|---|---|---|
| 1,590,558 | 6/1926 | Stenhouse | 137/624.15 |
| 3,507,297 | 4/1970 | Dann | 137/624.15 |
| 4,239,039 | 12/1980 | Thompson | 128/205.24 |
| 4,262,689 | 4/1981 | Rodder | 128/205.24 |

FOREIGN PATENT DOCUMENTS 8002183 10/1980 European Pat. Off. ....... 137/624.15

Primary Examiner—Henry J. Recla
Attorney, Agent, or Firm—Birch, Stewart, Kolasch & Birch

[57] ABSTRACT

Apparatus for artificial pulmonary ventilation during anaesthesia and resuscitation in which the gaseous transfer occurs by diffusion. The apparatus which is highly reliable, has a long working life, and achieves more active alveolar exchange, includes an on-off valve in a line for supplying air to the lungs. The valve has a valve body, a shutter seat in the body, respective air inlet and outlet ports in the valve body which open into the seat, a shutter sealingly rotatable in the seat under the action of drive means, and at least one duct in the shutter for interconnecting the ports periodically in accordance with the rotation of the shutter.

2 Claims, 7 Drawing Figures

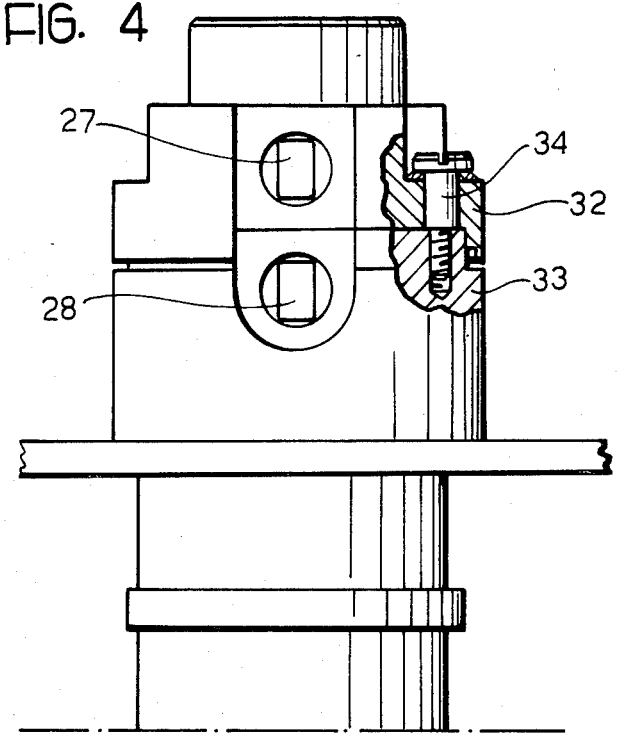
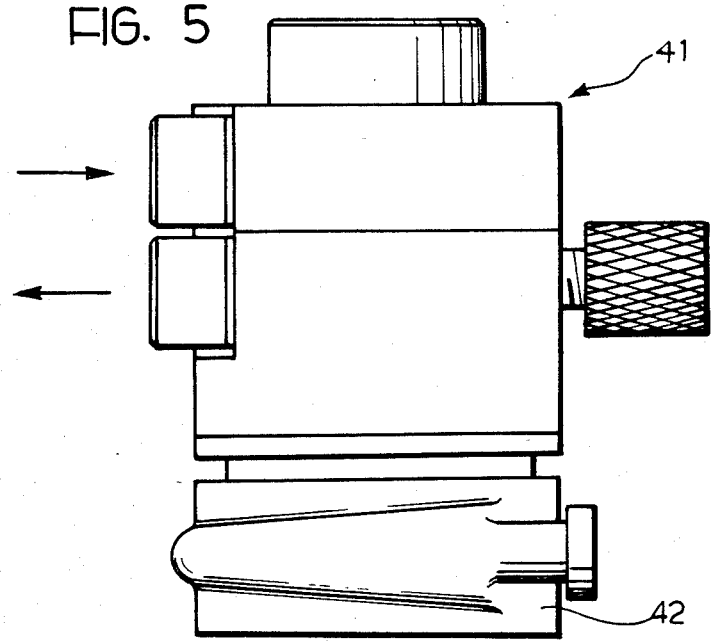

APPARATUS FOR ARTIFICIAL PULMONARY VENTILATION DURING ANAESTHESIA AND RESUSCITATION

The present invention relates to apparatus for artificial pulmonary ventilation during anaesthesia and resuscitation.

As is known, during anaesthesia and resuscitation, it is necessary to carry out artificial pulmonary ventilation on a patient when natural respiration is inactive or in any way insufficient. This ventilation essentially involves supplying the patient's lungs with air, which may be humidified, enriched with oxygen or mixed with anaesthetic gases, as necessary.

At present, there are basically two different techniques available for carrying out this ventilation.

According to a first method, excess external pressure is established in a certain rhythym which is approximately equal to the natural respiratory rhythym or is synchronised therewith. For the entire time during which this excess pressure is maintained there is a real transport of air into the lungs, this commonly being called "mass transport" or "bulk transport"; on cessation of the excess pressure there is a similar transport in the opposite direction. The control of the ventilation may be effected by controlling the pressure or the volume of the air supplied.

This method has several disadvantages: for example, the excess pressure disturbs the cardiac output, hindering the circulation of blood, compresses the blood in the pulmonary alveoli, and may cause pulmonary lesions (barotrauma) in patients with fibrous pulmonary tissue. Moreover, it does not allow surgical operations to be carried out on the trachea because of the rhythymic movement caused therein.

According to a second method, the transport of air, and particularly the transport of oxygen towards the pulmonary alveoli and the removal of carbon dioxide from the alveoli, is effected by diffusion ("diffusion transport"). In order to ensure a sufficient rate of diffusion, however, it is necessary to establish an oscillation of the air at a suitable frequency. In apparatus presently available for carrying out this method, the air is oscillated by periodically stopping a flow of pressurized air in a supply line by means of a solenoid valve. The flow of air is thus interrupted, resulting in the creation of a succession of wave fronts, and hence an oscillation proper. Although advantageous in that it is free from the disadvantages mentioned above, this ventilation apparatus still has only limited use.

Above all, it requires very frequent replacement of the solenoid valve which, because of the frequency of operation, is subject to very heavy use and soon reaches the end of its working life. A second disadvantage lies in the fact that the frequency of oscillation which may be imparted to the air is relatively low because of the limits on the frequency with which the solenoid valve may be energised and de-energised.

The object of the present invention is that of devising apparatus of the type specified above, which has structural and functional characteristics such as to overcome the disadvantages mentioned above with reference to the prior art.

This problem is solved by apparatus of the type specified, which is characterised in that it includes an on-off valve in the line for supplying air to the lungs, which has a valve body, a shutter seat in the body, respective air inlet and outlet ports in the valve body which open into the seat, a shutter sealingly rotatable in the seat under the action of drive means, and at least one duct in the shutter for periodically interconnecting the ports in accordance with the rotation of the shutter.

Further characteristics and advantages of the apparatus according to the present invention will emerge from the following description of a preferred embodiment, given by way of non-limiting example with reference to the appended drawings, in which:

FIG. 4 is a side view of the valve of FIG. 2;

FIG. 5 shows a variant of the valve of FIG. 2;

Figure 1:
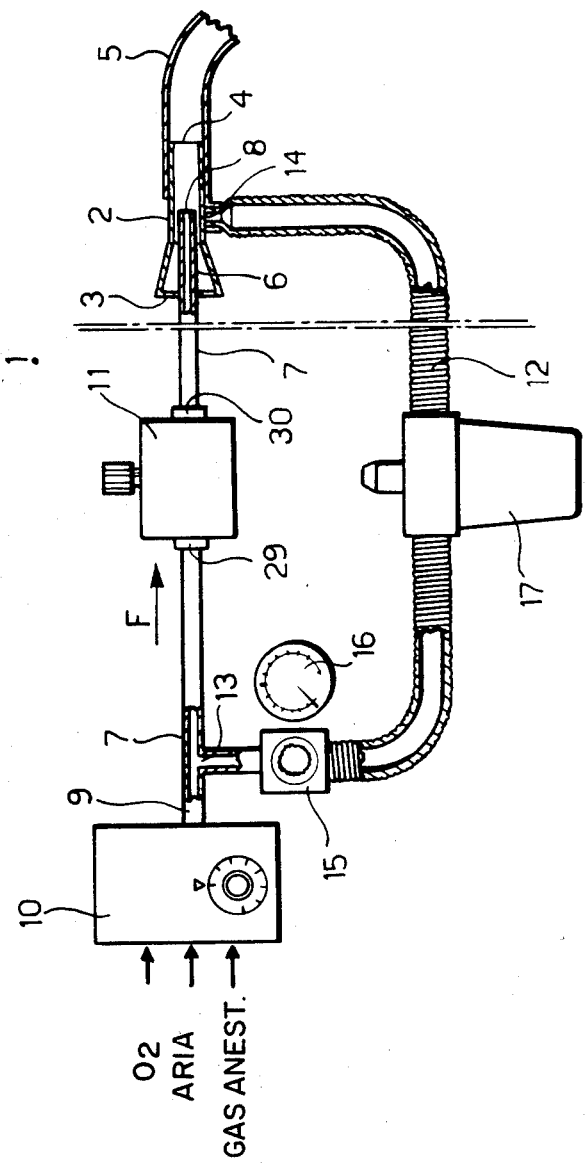
FIG. 1 is a schematic view of apparatus according to the invention.

With reference to the appended drawings, apparatus for artificial pulmonary ventilation during anaesthesia and resuscitation is generally indicated 1.

As will be clarified in the description below, this apparatus is based on the diffusion method and, more particularly, is of the high frequency jet ventilation (HFJV) type.

The apparatus 1 includes a Venturi tube 2 with an opening 3 which communicates with the environment and an opening 4 for connection to the thoracic cavity of a patient through an endotracheal tube 5.

Within the Venturi tube 2 is located coaxially the end 6 of an air supply line 7 with a mouth 8 which opens into the constriction of the Venturi tube 2 to act as a jet nozzle.

The opposite end 9 of the line 7 is connected to a mixer 10 in which the air is enriched with oxygen or mixed with anaesthetic gases, as required.

The line 7, through which air flows in the direction of arrow F, includes an on-off valve 11 which will be described in detail below.

A tube 12 branches from the line 7 at a point 13 upstream of the on-off valve 11 and opens into the Venturi tube 2 through an aperture 14 formed in the wall of the tube substantially in the constriction.

A pressure reducing valve 15, its pressure gauge 16, and a humidifier 17 are located in succession along the tube 12.

The on-off valve 11 includes a valve body 18 in which a cylindrical shutter seat with an axis X—X is formed. Within the seat 19 is housed a shutter 20 which is sealingly rotatable in the seat 19 about the axis X—X under the action of drive means, generally indicated 21, including a variable-speed electric motor 22.

In particular, the shutter 20 is supported by bearings 23, 24 and is retained axially by respective retaining rings 25, 26 housed in the valve body 18.

Two inlet and outlet ports 27, 28 provided with respective connectors 29, 30 are formed in the valve body 18 and have rectangular openings into the shutter seat 19 aligned substantially in the direction X—X.

The shutter 20 is provided with four ducts, each indicated 31, which are formed at regular intervals around the periphery of the shutter and extend in the direction X—X for such a length as to take in the two ports 27, 28.

The body 18 is formed in two parts 32, 33 which are juxtaposed in a plane perpendicular to the axis X—X. The parts 32, 33 carry the respective ports 27, 28 and are angularly displaceable to move these ports out of alignment with each other.

The two parts 32, 33 are maintained in juxtaposition by two screws 34, 35 which are captive in the part 33 and are engaged with two slots 36, 37 formed in the part 32.

A knob 38 is fixed rotatably on the part 33 and is provided with a pinion 39 which is engaged with toothing 40 formed on the part 32 to cause the relative angular displacement of the parts 32, 33.

The operation of the apparatus 1 is described below.

From the mixer 10, the air is directed through the line 7 towards the Venturi tube 2. When the flow of air passes through the on-off valve 11 the motor 22 of which is rotated at a predetermined angular velocity, it is periodically interrupted and hence, so to speak, broken. In fact, the inlet port 27 and the outlet port 28 are periodically interconnected by the ducts 31, when the latter are brought into positions facing the ports 27, 28 by the rotation of the shutter.

Clearly, in addition to the angular velocity of the duration of this connection also depends on the transverse dimensions of the ports 27, 28 and the ducts 31 together with the relative positioning of the two ports 27, 28 which are more or less out of alignment with each other.

It is possible to vary the non-alignment of the two ports by means of the knob 38 and thus vary the duration of the connection.

The duration of the connection is chosen according to a desired periodic distribution of the duration of the connection and of the interruption. Normally, it is arranged that the duration of the connection is less than that of the interruption, so as to favour the diffusion of carbon dioxide leaving the lungs relative to the diffusion of the entering oxygen. For example, it is arranged that, in the entire period, about 40% thereof comprises connection and about 60% interruption.

The flow of air which is interrupted in this way reaches the Venturi tube 2 where it mixes with the flow of suitably humidified air coming from the tube 12. The mixture thus obtained is then placed at the disposal of the patient's lungs by means of the endotracheal tube 5. The oscillation of the mixture in the entire volume of the lungs is maintained by the interrupted flow from the mouth 8 of the line 7, these oscillations favouring the gaseous diffusion of the gases within the volume of the lungs, and thus favouring the transport of oxygen into the lungs as well as the removal of carbon dioxide.

The apparatus according to the invention has the main advantage of high reliability and a long working life which are achieved essentially by virtue of the particular rotary operation of the on-off valve 11. In addition to this, with the apparatus according to the invention, the frequency of oscillation may be brought to very high values because of the ease with which the on-off valve 11 may be constructed with a very large number of ducts 31.

Figure 2:
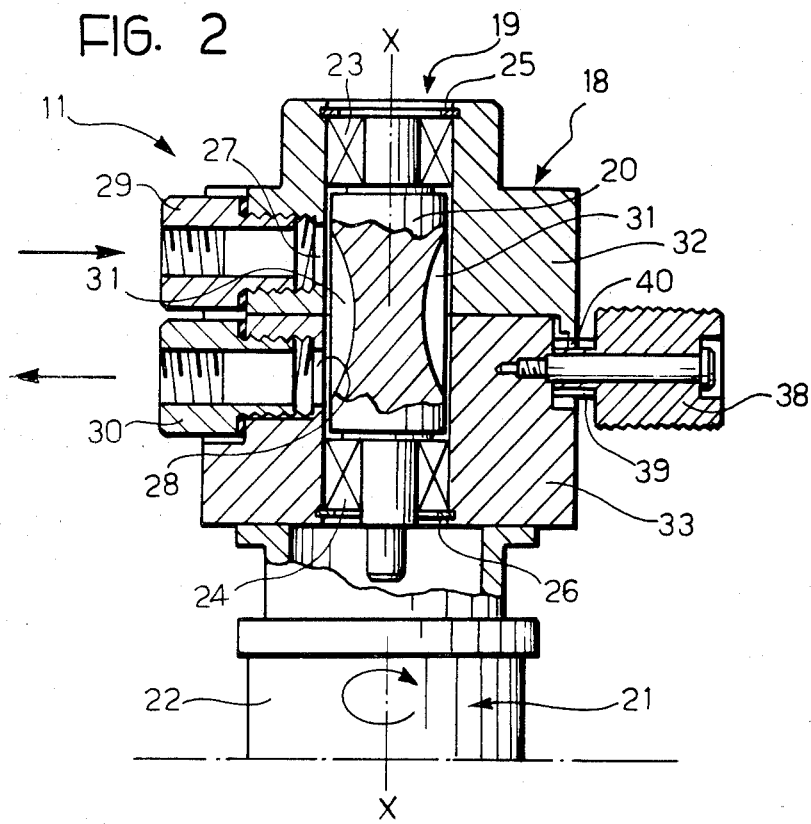
FIG. 2 is a partially sectioned elevational view of an on-off valve used in the apparatus of FIG. 1.
Figure 3:
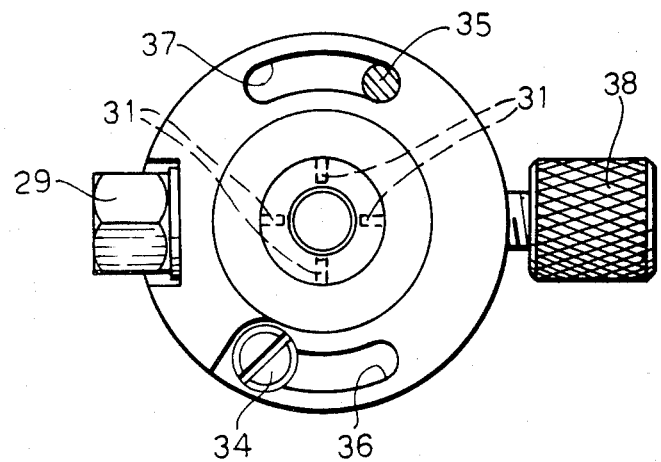
FIG. 3 is a plan view of the valve of FIG. 2.

FIG. 5 shows an on-off valve 40 which is a variant of the on-off valve 11 of FIG. 2. In FIGS. 1 and 5, similar parts are indicated by the same reference numerals. In the valve 41, the drive means for rotating the shutter 20 comprise an air turbine 42 supplied with compressed air in a conventional manner.

By virtue of this variation, the ventilating apparatus according to the invention has the advantage, which is appreciable in some situations, of complete independence from the main supply and hence has greater versatility in use.

Figure 6:
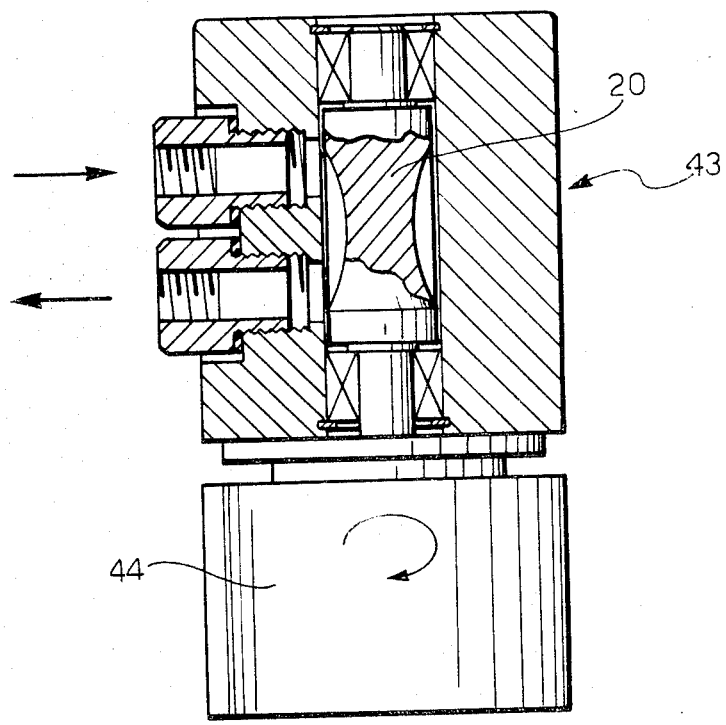
FIG. 6 shows a further variant of the valve of FIG. 2.
Figure 7:
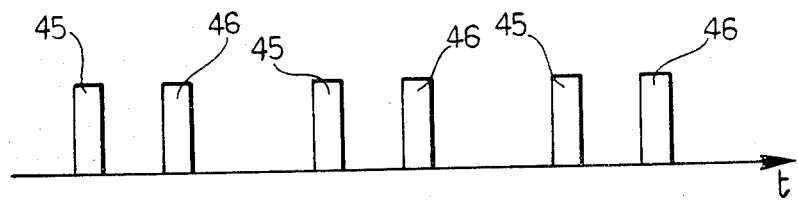
FIG. 7 is a diagram of the control pulses imparted to the valve of FIG. 6.

FIG. 6 shows an on-off valve 43 which is a further variant of the on-off valve 11 of FIG. 1. In FIGS. 1 and 6, similar parts have been indicated by the same reference numerals. In the on-off valve 43, the valve body is a single piece and the shutter is rotated in steps by a stepping motor 44 controlled in a conventional manner by a train of pulses, shown in FIG. 7, from a pulse generator, not shown since it is conventional. In particular, the shutter is positioned step by step by the stepping motor so that the ports 27, 28 face or do not face a duct 31. The pulses which cause the rotation of the shutter into a position in which the ports 27, 28 face a duct 31 are indicated 45, while the pulses which cause the rotation of the shutter into a position in which the ports 27, 28 do not face duct 31 are indicated 46.

The time interval between the pulse 46 and the preceding pulse 45 represents the duration of the connection between the ports 27, 28 and a duct 31, while the time interval between the same pulse 46 and the subsequent pulse 45 represents the duration of the interruption. By suitable phasing of the pulse 46 and the pulses 45, through simple manipulation of the pulse generator, it is possible to obtain the desired periodic distribution between the duration of the connection and the duration of the interruption.

By virtue of this further variation, the on-off valve 45 is more robust and simpler to construct, and the desired distribution between the duration of the connection and the duration of the interruption is easily achieved by acting electrically on the pulse generator.

I claim:

1. Apparatus for effecting gaseous transfer by diffusion for artificial pulmonary ventilation during anaesthesia and resuscitation, comprising:

a supply line for supplying air to the lungs; an alternately openable and closable valve in said supply line for intermittently stopping and permitting flow of air through said supply line for generating pressure fluctuations in said air;

said valve comprising a valve body having two parts rotatably attached to each other about a central axis, a shutter seat defined across said two parts, an inlet port in one of said two body parts open to said shutter seat and connected to said supply line for supplying air to said valve, and an outlet port in the other of said two body parts and open to said shutter seat for releasing air from said valve;

a shutter rotatably mounted in said valve body about said central axis and sealingly engaged with said two parts across said shutter seat for closing said inlet and outlet ports;

a variable speed electric motor including means for rotating said shutter over said seat;

at least one duct in said shutter for intermittently connecting said inlet and outlet ports for permitting flow of air through said valve; and means for adjusting the relative angular positions of said first and second body parts and said inlet and outlet ports about the axis of rotation of said shutter for adjusting the frequency of said fluctuations and the period during which air is permitted to flow through said valve to the lungs.

2. Apparatus for effecting gaseous transfer by diffusion for artificial pulmonary ventilation during anaesthesia and resuscitation, comprising:

a supply line for supplying air to the lungs;

an alternately openable and closable valve in said supply line for intermittently stopping and permitting flow of air through said supply line for generating pressure fluctuations in said air;

said valve comprising a valve body having two parts rotatably attached to each other about a central axis, a shutter seat defined across said two parts, an inlet port in one of said two body parts open to said shutter seat and connected to said supply line for supplying air to said valve, and an outlet port in the other of said two body parts and open to said shutter seat for releasing air from said valve;

a shutter rotatably mounted in said valve body about said central axis and sealingly engaged with said two parts across said shutter seat for closing said inlet and outlet ports;

a turbine including means for rotating said shutter over said seat;

at least one duct in said shutter for intermittently connecting said inlet and outlet ports for permitting flow of air through said valve; and means for adjusting the relative angular positions of said first and second body parts and said inlet and outlet ports about the axis of rotation of said shutter for adjusting the frequency of said fluctuations and the period during which air is permitted to flow through said valve to the lungs.

* * * * *